United States Patent
Vandegriff et al.

(10) Patent No.: US 8,021,858 B2
(45) Date of Patent: Sep. 20, 2011

(54) METHOD FOR MAKING POLYALKYLENE OXIDE MODIFIED HEMOGLOBIN

(75) Inventors: Kim D. Vandegriff, San Diego, CA (US); Ashok S. Malavalli, San Diego, CA (US); Gnel M. Mkrtchyan, La Mesa, CA (US)

(73) Assignee: Sangart, Inc., San Diego, CA (US)

( * ) Notice: Subject to any disclaimer, the term of this patent is extended or adjusted under 35 U.S.C. 154(b) by 142 days.

(21) Appl. No.: 12/536,842

(22) Filed: Aug. 6, 2009

(65) Prior Publication Data
US 2010/0075379 A1 Mar. 25, 2010

Related U.S. Application Data

(60) Provisional application No. 61/099,092, filed on Sep. 22, 2008.

(51) Int. Cl.
*C12P 21/00* (2006.01)
(52) U.S. Cl. .................. 435/69.6; 530/385; 435/71.1

(58) Field of Classification Search .................. 530/385; 435/69.6, 71.1
See application file for complete search history.

(56) References Cited

U.S. PATENT DOCUMENTS

| | | | | |
|---|---|---|---|---|
| 5,234,903 A | * | 8/1993 | Nho et al. | 514/13.4 |
| 6,017,943 A | * | 1/2000 | Acharya et al. | 514/410 |

* cited by examiner

*Primary Examiner* — Chih-Min Kam
(74) *Attorney, Agent, or Firm* — The Nath Law Group; Laurie A. Axford (57) ABSTRACT

The present invention is a method for preparing a hemoglobin based oxygen carrier to deliver oxygen to tissue. The method comprises mixing a deoxygenated hemoglobin with a maleimide-activated polyakylene oxide (PAO) to obtain an oxygen carrying product. This product is characterized as having 2 to about 8 PAO moieties covalently bound to a deoxygenated hemoglobin and a p50 less than native stroma-free hemoglobin from the same animal source when measured under the same conditions.

5 Claims, 4 Drawing Sheets

METHOD FOR MAKING POLYALKYLENE OXIDE MODIFIED HEMOGLOBIN

CROSS-REFERENCE TO RELATED APPLICATIONS

This application claims priority benefit of U.S. provisional patent application Ser. No. 61/099,092 filed Sep. 22, 2008, which is incorporated by reference in its entirety.

TECHNICAL FIELD

The present invention relates to hemoglobin based oxygen carriers (HBOCs), and more particularly to methods for making polyalkylene oxide (PAO) modified hemoglobin conjugates having a high affinity for oxygen and improved conjugate characteristics.

BACKGROUND OF THE INVENTION

Oxygen carriers that are useful, for example, as blood substitutes (sometimes referred to as "oxygen-carrying plasma expanders") can be grouped into the following three categories: i) perfluorocarbon-based emulsions, ii) liposome-encapsulated hemoglobin, and iii) modified hemoglobin. As discussed below, none has been entirely successful, though products comprising modified cell-free hemoglobin are thought to be the most promising. Perfluorochemical-based emulsions dissolve oxygen as opposed to binding it as a ligand. In order to be used in biological systems, the perfluorochemical must be emulsified with a lipid, typically egg-yolk phospholipid. Though the perfluorocarbon emulsions are inexpensive to manufacture, they do not carry sufficient oxygen at clinically tolerated doses to be effective. Conversely, while liposome-encapsulated hemoglobin has been shown to be effective, it is too costly for widespread use. (See generally, Winslow, Robert M., *Hemoglobin-based Red Cell Substitutes*, Johns Hopkins University Press, Baltimore, Md. (1992)).

Initial attempts to utilize free hemoglobin from erythrocyte hemolysates as a red cell substitute were unsuccessful. The stromal components were found to be toxic, resulting in coagulopathy and associated renal failure. In 1967, stroma-free hemoglobin solutions had been prepared (Rabiner et al., J. Exp. Med. 126:1127 (1967)). However, stroma-free hemoglobin was found to have a relatively short transfusion half-life of only about 100 minutes The reason for the short circulation half-life of stroma-free hemoglobin is due to the ability of the protein to disassociate from its tetrameric form into dimers that are rapidly filtered from the circulation by the kidneys. Accordingly, a multitude of methods for cross-linking hemoglobin to prevent dissociation have been devised to minimize the extravasation of hemoglobin. Internally cross-linked hemoglobin (intramolecularly cross-linked) formed by binding amino acid residues between subunits may be achieved with diaspirin (diesters of bis-3,5-dibromosaliocylate, U.S. Pat. No. 4,529, 719) or using 2-N-2-formyl-pyridoxal-5'-phosphate and borohydride (Benesch et al., Biochem. Biophys. Res. Commun. 62:1123 (1975)). Intramolecular cross-linking that chemically binds subunits of the tetrameric hemoglobin unit to prevent the formation of dimers is disclosed in U.S. Pat. No. 5,296,465. Simon S. R. and Konigsberg W. H. disclosed the use of bis (N-maleimidomethyl) ether (BME) to generate intramolecular cross-linked hemoglobin (*PNAS* 56:749-56, (1966)) that was reported to have a four fold increase in half-life when infused into rats and dogs (Bunn, H. F. et al., J. Exp. Med. 129:909-24 (1969)). However, the cross-linking of hemoglobin with BME resulted in the concomitant increase in the oxygen affinity of hemoglobin which at the time was thought to prevent its use as a potential hemoglobin-based oxygen carrier.

Although crosslinked hemoglobins demonstrate longer half lives, these compounds still have a propensity to cause vasoconstriction, which may manifest as hypertension in animals and man (Amberson, W., Science 106: 117-117 (1947); and Keipert, P. et al., Transfusion 33: 701-708, (1993)). Human hemoglobin cross-linked between a chains with bis-dibromosalicyl-fumarate (ααHb) was developed by the U.S. Army as a model red cell substitute, but was abandoned by the Army after demonstration of severe increases in pulmonary and systemic vascular resistance (Hess, J. et al., Blood 78: 356A (1991)). A commercial version of this product was also abandoned after a disappointing Phase III clinical trial (HemAssist™ Baxter International, Inc., Deerfield, Ill.; see Winslow, R. M., Vox sang 79: 1-20 (2000)).

The most commonly advanced explanation for the vasoconstriction produced by cell-free hemoglobin is that it readily binds the endothelium-derived relaxing factor, nitric oxide (NO). Three molecular approaches have been advanced in attempting to overcome the NO binding activity of hemoglobin.

The first approach was utilizing recombinant DNA which attempted to reduce the NO binding of hemoglobin by site-specific mutagenesis of the distal heme pocket (Eich et al., Biochem. 35:6976-83 (1996)). Recombinant hemoglobins with reduced affinity for NO have been produced that are less hypertensive in top-load rat experiments (Doherty, D. H. et al., Nature Biotechnology 16: 672-676 (1998); and Lemon, D. D. et al., Biotech 24: 378 (1996)). However, studies suggest that NO binding may not be the only explanation for the vasoactivity of hemoglobin.

The second approach utilized chemical modification in which the size of the hemoglobin was enhanced through oligomerization, which attempted to reduce or possibly completely inhibit the extravasation of hemoglobin from the vascular space into the interstitial space (Hess J. R. et al., J. Appl. Physiol. 74:1769-78 (1978); Muldoon S. M. et al., J. Lab. Clin. *Med.* 128:579-83 (1996); Macdonal V. W. et al., Artificial Cells, Blood Substitutes and Immobilization Biotechnology 22:565-75 (1994); Furchgott, R. Ann. Rev. Pharmacol. 24:175-97 (1984); and Kilbourne R. et al., Biochem. Biophys. Res. Commun. 199:155-62 (1994)). Cross-linking stroma-free hemoglobin to form poly-hemoglobin is also described in U.S. Pat. Nos. 4,001,200; and 4,001,401.

The third approach involved surface modification of the hemoglobin. Surface modification of hemoglobin involves covalently attaching macromolecules to the reactive groups on the surface of the hemoglobin, such as dextran (Chang J. E. et al., Can. J. Biochem. 55:398 (1977)), hydroxyethyl starch (DE 2,161,086); gelatin (DE 2,449,885); albumin (DE 2,449, 885) and polyethylene glycol (DE 3,026,398; U.S. Pat. Nos. 4,670,417; 4,412,989; and 4,301,144).

It has been found that large, surface modified hemoglobin, such as those modified with polyethylene glycol (PEG), were virtually free of the hypertensive effect, even though their NO binding rates were identical to those of the severely hypertensive ααHb (Rohlfs, R. J. et al., J Biol Chem 273: 12128-12134 (1998)). Furthermore, it was found that PEG-hemoglobin was extraordinarily effective in preventing the consequences of hemorrhage when given as an exchange transfusion prior to hemorrhage (Winslow, R. M. et al., J. Appl. Physiol. 85: 993-1003 (1998)).

Conjugation of PEG to hemoglobin also reduces its antigenicity and extends its half-life in circulation. However, the PEG-conjugation reaction has resulted in dissociation of the hemoglobin tetramer into monomer subunits causing gross hemoglobinuria in exchange-transfused rats receiving PEG-conjugates of hemoglobin monomeric units below 40,000 Daltons (Iwashita and Ajisaka, *Organ-Directed Toxicity: Chem. Indicies Mech., Proc. Symp.*, Brown et al., Eds. Pergamon, Oxford, England pgs 97-101 (1981)). A polyalkylene oxide conjugated hemoglobin having a molecular weight greater than 84,000 Daltons was prepared by Enzon, Inc. (U.S. Pat. No. 5,650,388) that carries 10 copies of PEG-5000 chains linked to hemoglobin at its α and ε-amino groups. This degree of substitution was described as avoiding clinically significant nephrotoxicity associated with hemoglobinuria in mammals.

A variety of linkers and methods have been developed for conjugating macromolecules to hemoglobin. Phenyl-based moieties such as 4-phenylmaleimido or 3-phenylmaleimido have been used successfully to conjugate PEG to hemoglobin (U.S. Pat. No. 5,750,725). However, the use of phenyl groups in therapeutic agents is believed by some to be undesirable.

Polyalkylene oxides that do not contain these phenyl groups were prepared having a succinimidyl functional group for binding free ε-amines available on the surface of the hemoglobin (Larwood and Szoka, *J. Labelled Compounds Radiopharm.* 21:603-14 (1984)). However, the ester bond formed between the polyalkylene chain and the succinimidyl group was found to be easily hydrolyzed in the living body. To address this issue, polyalkylene oxides were activated to produce urethane linkages with ε-amino groups of hemoglobin, which are less susceptible to hydrolytic degradation (U.S. Pat. No. 5,234,903). Other methods have been utilized that employ thiolation of the ε-amines of hemoglobin for binding polyalkylene oxides having maleimide functional groups (U.S. Pat. No. 6,844,317). The thioester bonds formed between the polyalkylene chain and the maleimido group are less susceptible to degradation (U.S. Patent Application No. 2006/0135753).

Conjugation of hemoglobin to polyalkylene oxides has been performed in both the oxygenated and deoxygenated states. U.S. Pat. No. 6,844,317 describes conjugating hemoglobin in the oxygenated or "R" state to enhance the oxygen affinity of the resultant hemoglobin. This is accomplished by equilibrating the hemoglobin with the atmosphere prior to conjugation. Others describe a deoxygenation step prior to conjugation to diminish the oxygen affinity and increase structural stability to withstand the physical stresses of chemical modification, diafiltration and/or sterile filtration and sterilization (U.S. Pat. No. 5,234,903). For intramolecular cross-linking of hemoglobin, it is suggested that deoxygenating the hemoglobin prior to modification may be required to expose Lys 99 of the alpha chain to the amino group-reactive cross-linking reagent (U.S. Pat. No. 5,234,903).

In all the aforementioned methods for surface modifying hemoglobin, the results in terms of conjugation location, efficiency and ultimate conjugate characteristics have been highly unpredictable. For example, the effects of conjugation conditions on the conformation and surface availability of reactive groups on the hemoglobin molecule, as well as the ability of such reactive groups to form stable bonds with linking groups on macromolecules is highly specific to the reactants and the method, and not easily predicted without significant experimentation. In addition, the effects of surface decoration on the ultimate stability, oxygen affinity, vasoactivity and other performance characteristics of the conjugate must be carefully considered.

Accordingly, improved methods for efficiently producing PAO-Hb conjugates with desirable properties are needed. Such PAO-Hb conjugates will preferentially exhibit a high affinity for oxygen, efficiently deliver oxygen to tissues, not be prematurely excreted from the system, be stable and, unlike whole blood, be stored at room temperature. Such conjugates would eliminate the current need for blood type and cross-matching currently performed for blood transfusions and can be easily and economically manufactured.

BRIEF SUMMARY OF THE INVENTION

The present invention provides methods for preparing a PAO-Hb conjugate that is useful for, inter alia, delivering oxygen to tissue. One particularly preferred method comprises the step of mixing a deoxygenated hemoglobin from red blood cells with a maleimide-activated polyalkylene oxide (PAO) to obtain an oxygen carrying conjugate. This product is characterized by having 2 to about 8 PAO moieties covalently bound to deoxygenated hemoglobin and a p50 less than native stroma-free hemoglobin from the same animal source when measured under the same conditions.

In one aspect of the present invention, the PAO is a polyethylene oxide of the formula: $((CH_2CH_2O)_n)$, a polypropylene oxide of the formula: $((CH(CH_3)CH_2O)$ a polyethylene/polypropylene oxide copolymer of the formula: $((CH_2CH_2O)_n-(CH(CH_3)CH_2O)_n)$ or a polyethylene glycol (PEG) of the formula: $HO(CH_2CH_2O)_nH$ wherein n is greater than or equal to 4. In one embodiment of this aspect of the invention the PAO has a molecular weight of 1,000 Daltons to about 20,000 Daltons.

In another embodiment of this aspect of the invention the PAO is a maleimide-activated PEG of the formula:

Y—R—[CH$_2$CH$_2$O]$_n$—CH$_2$CH$_2$—OCH$_3$ wherein Y is a maleimido activated moiety, R is a linker and n is greater than or equal to 4. The R linker may also be absent (i.e. there is a direct bond between Y and —CH$_2$—). When R is present, it may be an alkyl, an amide, a carbamate or a phenyl group. If R is an alkyl group, it is preferably a methyl group or an alkyl group of from two to six carbon atoms.

In another aspect of the present invention the hemoglobin of the PAO-Hb conjugate is obtained from a human, a cow, or a pig. Other aspects of the present invention are described throughout the specification.

DETAILED DESCRIPTION OF THE INVENTION

The present invention is directed to methods of making HBOCs in the form of PAO-Hb conjugates having high oxygen affinity that are more stable against auto-oxidation and formation of unmodified hemoglobin dimers. For certain applications, these compositions are capable of delivering oxygen to tissues more efficiently than compositions with oxygen affinities that approximate native hemoglobin in whole blood and can be produced and stored for long periods of time without requirements for refrigeration or freezing. The product may even be stable at higher temperatures and subjected to virus inactivation by pasteurization.

For use in the present invention, the PAO-Hb conjugate will have an oxygen affinity that is greater than whole blood, and preferably twice that of whole blood, or alternatively, greater than that of stroma-free hemoglobin (SFH), when measured under the same conditions. In most instances, this means that the PAO-Hb conjugate will have a p50 less than 10 Torr but above 3 Torr. In the free state, SFH has a p50 of approximately 15 Torr, whereas the p50 for whole blood is approximately 28 Torr.

It was previously suggested that increasing oxygen affinity of an HBOC, and thereby lowering the p50 such as described herein might actually enhance delivery of oxygen to tissues. (See U.S. Pat. No. 6,974,795.) At the time, this suggestion contradicted the widely held belief that modified hemoglobins for use as blood substitutes should have oxygen affinities that were no greater than that of whole blood. However, high oxygen affinity is now regarded as a desirable property.

One method for making PAO-Hb conjugates with high oxygen affinity involves thiolating oxygenated hemoglobin and then reacting with maleimidyl activated PAO (U.S. Pat. No. 6,974,795.) This was believed to be necessary to achieve a conjugation product with a desirable molecular volume and stability to auto-oxidation. However, the necessity for a separate thiolation step complicates the manufacturing process. Accordingly, the Hb starting material in the process of the present invention is "unthiolated hemoglobin."

Definitions

Unless defined otherwise, all terms used herein have the same meaning as are commonly understood by one of skill in the art to which this invention belongs. In the event that there is a plurality of definitions for a term herein, those in this section prevail.

The term "hemoglobin" or "Hb" as used herein refers generally to the protein contained within red blood cells that transports oxygen. Each molecule of hemoglobin has 4 subunits, 2 α-chains and 2 β-chains, which are arranged in a tetrameric structure. Each subunit also contains one heme group, which is the iron-containing center that binds oxygen. Thus, each hemoglobin molecule can bind 4 oxygen molecules. As used herein, this term by itself refers both to native, unmodified hemoglobin, as well as modified hemoglobin.

The term "modified hemoglobin" as used herein includes, but is not limited to, hemoglobin altered by a chemical reaction such as intra- (subunit to subunit) and inter- (tetramer to tetramer) molecular cross-linking and genetic manipulation.

The term "unthiolated hemoglobin" as used herein refers generally to hemoglobin that has not undergone a thiolation reaction to introduce thiol groups. Accordingly, "unthiolated hemoglobin" has only thiol groups associated with cysteine residues in the hemoglobin primary structure.

The term "conjugated hemoglobin" as used herein refers to hemoglobin described above to which chemical groups such as dextran or polyalkylene oxide have been attached, most usually covalently attached to the exposed amino acid side chains on the surface of the hemoglobin molecule. These may be side chains naturally occurring on the hemoglobin.

The term "stroma-free hemoglobin" or "SFH" as used herein refers to hemoglobin from which all red blood cell membranes have been removed.

The term "methemoglobin" as used herein refers to an oxidized form of hemoglobin that contains iron in the ferric state and cannot function as an oxygen carrier.

Figure 1:
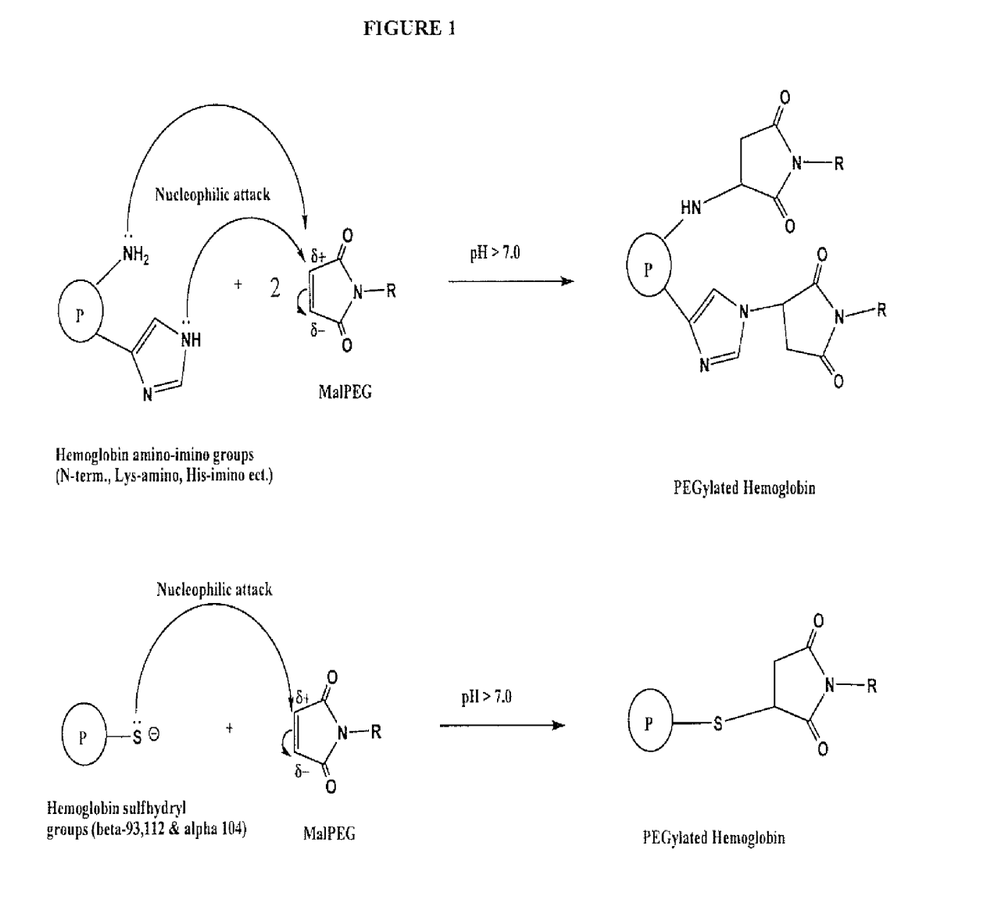
FIG. 1 shows the chemistry for maleimide reactions with amino, imino, and thiol groups.
Figure 2:
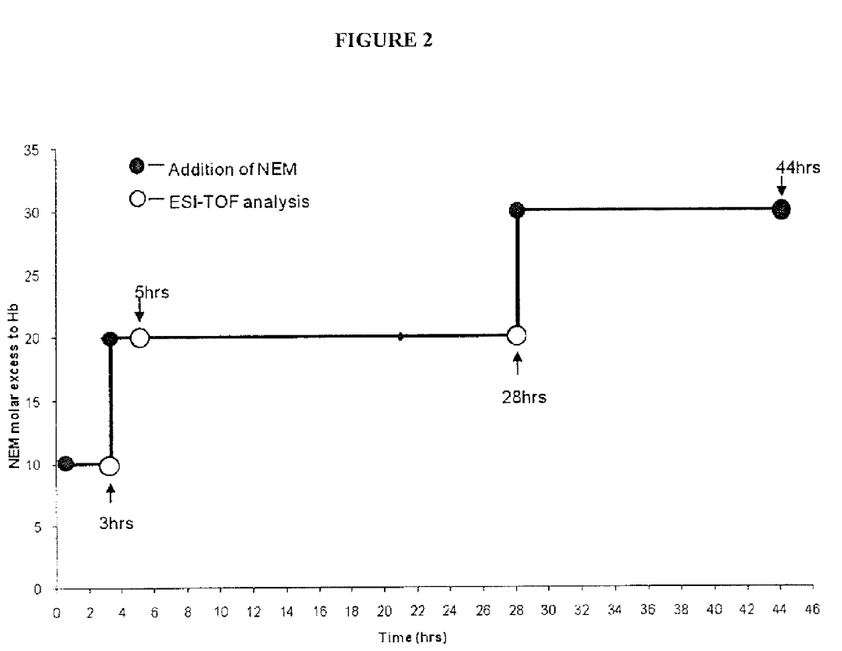
FIG. 2 shows the reaction scheme for the N-ethylmaleimide (NEM) reaction with deoxyHb to determine the sites of modification.

The term "MalPEG-Hb" as used herein refers to hemoglobin to which malemidyl-activated PEG has been conjugated. Such MalPEG-Hb may be further referred to by the following formula:

where Hb refers to hemoglobin, Y' is thiol, amino and/or imino group on the surface of Hb, Y is a succinimido covalent linkage that results from reacting Hb with MalPEG, R is absent or is a linker comprising a alkyl, amide, carbamate or phenyl group (depending on the source of raw material and the method of chemical synthesis), $[CH_2-CH_2-O]_n$ are the oxyethylene units making up the backbone of the PEG polymer, where n defines the length of the polymer and X is a terminal group, which may include methoxy, protected hydroxyl, acetal, alkenyl, amine, protected amine, methoxy 2-propanol, monoethyl ether, monobenzylether, dibenzylmethylene, and dimethlamine, where m defines number of conjugated PEG molecules/Hb tetramer. The reaction scheme is shown in FIG. 1.

The term, "polyalkylene oxide" or "PAO" as used herein refers to suitable synthetic hydrophilic polymers such as PEG, POE, polypropylene oxide or a polyethylene/polypropylene oxide copolymer. Other straight, branched chain and optionally substituted synthetic polymers that would be suitable in the practice of the present invention are well known in the medical field.

The term "oxygen carrying capacity", or simply "oxygen capacity" as used herein refers to the capacity of a blood substitute to carry oxygen, but does not necessarily correlate with the efficiency in which it delivers oxygen. Oxygen carrying capacity is generally calculated from hemoglobin concentration, since it is known that each gram of hemoglobin binds 1.34 ml of oxygen. Thus, the hemoglobin concentration in g/dl multiplied by the factor 1.34 yields the oxygen capacity in ml/dl. Hemoglobin concentration can be measured by any known method, such as by using the β-Hemoglobin Photometer (HemoCue, Inc., Angelholm, Sweden). Similarly, oxygen capacity can be measured by the amount of oxygen released from a sample of hemoglobin or blood by using, for example, a fuel cell instrument (e.g., Series 800 Oxygen Analyzers, Illinois Instruments, Inc, Model 810, Johnsburg, Ill.).

The term "oxygen affinity" as used herein refers to the avidity with which an oxygen carrier such as hemoglobin binds molecular oxygen. This characteristic is defined by the oxygen equilibrium curve which relates the degree of saturation of hemoglobin molecules with oxygen (Y axis) with the partial pressure of oxygen (X axis). The position of this curve is denoted by the value, p50, the partial pressure of oxygen at which the oxygen carrier is half-saturated with oxygen, and is inversely related to oxygen affinity. Hence the lower the p50, the higher the oxygen affinity. The oxygen affinity of whole blood (and components of whole blood such as red blood cells and hemoglobin) can be measured by a variety of methods known in the art. (See, e.g., Winslow et al., J. Biol. Chem. 252(7):2331-37 (1977)). Oxygen affinity may also be determined using a commercially available HEMOX™ Analyzer (TCS Scientific Corporation, New Hope, Pa.). (See, e.g., Vandegriff and Shrager in *Methods in Enzymology* (Everse et al., eds. 232:460 (1994)).

The term "hemoglobin based oxygen-carrying component" or "HBOC" as used herein refers broadly to a hemoglobin containing substance capable of carrying oxygen in the body's circulatory system and delivering at least a portion of that oxygen to the tissues. In preferred embodiments, the hemoglobin is conjugated to MalPEG.

The term "stable to autoxidation" as used herein refers to the ability of a HBOC to maintain a low rate of autoxidation. HBOC is considered stable at 24° C. if the methemoglobin/total hemoglobin ratio does not increase more than 2% after 10 hours at 24° C. For example, if the rate of auto-oxidation is $0.2\ hr^{-1}$, then if the initial percentage of methemoglobin is 5%, HBOC would be considered stable at room temperature for 10 hours if this percentage did not increase above 7%.

The term "methemoglobin/total hemoglobin ratio" as used herein refers to the ratio of ferric hemoglobin to total hemoglobin.

The term "mixture" as used herein refers to a mingling together of two or more substances without the occurrence of a reaction by which they would lose their individual properties; the term "solution" refers to a liquid mixture; the term "aqueous solution" refers to a solution that contains some water and may also contain one or more other liquid substances with water to form a multi-component solution; the term "approximately" refers to the actual value being within a range, e.g. 10%, of the indicated value.

The term "polyethylene glycol" as used herein refers to liquid or solid polymers of the general chemical formula $HO-(CH_2-CH_2O)_n-H$, where n is greater than or equal to 4. Any PEG formulation, substituted or unsubstituted, can be used.

The term "pharmaceutically acceptable diluent" as used herein refers to any diluent or excipient that is compatible with the other ingredients of the formulation, and which is not deleterious to the recipient. The pharmaceutically acceptable diluent can be selected on the basis of the desired route of administration, in accordance with standard pharmaceutical practices.

The term "carbamate group" as used herein refers to the group of the general formula: $-NR-(CO)C-$, wherein in R may be an alkyl group or preferably a hydrogen atom.

The term "phenyl group" as used herein refers to an aromatic ring structure of the general formula: $-(C_6R_4)-$, wherein all of the R groups are the same alkyl group, or each R group is a different alkyl group, wherein all of the R groups are alkyl groups and at least two of the alkyl groups are the same, or each of the R groups is a hydrogen atom, or wherein the R groups are a combination of alkyl groups and hydrogen atoms.

The term "alkyl group", as used herein by itself, or as part of another substituent refers to a straight, branched or cyclic hydrocarbon chain, including di- and multi-radicals, having the number of carbon atoms designated (i.e. $C_1$-$C_6$ means one to six carbons) and of the general form $-C_nH_{(2n+1)}-$. Alkyl groups include straight chain, branched chain or cyclic groups, with straight being preferred. Examples include methyl, ethyl, propyl, isopropyl, butyl, isobutyl, tert-butyl, pentyl, and neopentyl.

The term "amide group" as used herein refers to the group of the general formula: $-(C=O)NR-$, wherein in R may be an alkyl group or preferably a hydrogen atom.

The term "unsaturated aliphatic moiety" as used herein refers to carbon atoms bound together covalently wherein some of these bonds are double bonds.

The term "aromatic moiety" as used herein refers to a ring structure wherein some of the bonds binding the atoms of the ring are double bonds (i.e. conjugated ring of unsaturated bonds) and wherein the structure exhibits a stronger stabilization than would be expected by the presence of the double bonds or conjugation alone.

Hemoglobin

The hemoglobin for use in the present invention is derived from red blood cells. This means that the hemoglobin can either be isolated from red blood cells or it may be recombinantly produced based on hemoglobin-encoding genetic engineering. It may also be either native (unmodified) or chemically modified, such as intra- or intermolecular cross-linked hemoglobin. Human alpha- and beta-globin genes have both been cloned and sequenced. Liebhaber, et al., P.N.A.S. 77: 7054-7058 (1980); Marotta, et al., J. Biol. Chem. 353: 5040-5053 (1977) (beta-globin cDNA).

The present invention is not limited by the source of the hemoglobin. For example, the hemoglobin may be derived from non-human animals or humans. Preferred sources of hemoglobin for certain applications are humans, cows and pigs. The Hb of the present invention should be stroma free and endotoxin free.

Hemoglobin is known to exhibit autoxidation when it reversibly changes from the ferrous ($Fe^{2+}$) to the ferric ($Fe^{3+}$), i.e., methemoglobin form. When this happens, molecular oxygen dissociates from the oxyhemoglobin in the form of a superoxide anion ($O_2^-$). This can also result in destabilization of the heme-globin complex and eventual denaturation of the globin chains. Both oxygen radical formation and protein denaturation are believed to play a role in in vivo toxicity of HBOCs (Vandegriff, K. D., Blood Substitutes, Physiological Basis of Efficacy, pages 105-130, Winslow et al., ed., Birkhäuser, Boston, Mass. (1995)).

With most HBOCs, there is a negative correlation between oxygen affinity and hemoglobin oxidation, i.e., the higher the oxygen affinity, the lower the rate of auto-oxidation. However, the effects of different hemoglobin modifications on oxygen affinity and the rate of auto-oxidation are not always predictable. In addition, the optimal balance between oxygen affinity and auto-oxidation rate is not well understood.

Hemoglobin Conjugation

There are many different scientific approaches to manufacturing surface modified hemoglobin with high oxygen affinity (i.e. those with p50s less than SFH). For example, studies have identified the amino acid residues that play a role in oxygen affinity, such as β93 cysteine. The β93 cysteine residue is located immediately adjacent to the proximal β92 histidine residue, which is the only residue in beta subunits directly coordinated to the heme iron. Attachment of the rigid, bulky maleimide group to the β93 cysteine displaces a salt bridge that normally stabilizes the low-affinity T-state Hb conformation (Perutz et al., Biochemistry 13: 2163-2173 (1974)). This shifts the quaternary conformation towards the R state, resulting in higher $O_2$ affinity (Imai et al., Biochemistry 12:798-807 (1973)).

In the present method, the hemoglobin is conjugated by covalent attachment of maleimidyl activated polyalkylene oxide to the exposed amino acid side chains on the deoxygenated hemoglobin molecule. Conjugation is carried out principally to increase the molecular size of the hemoglobin, however, the conjugation method of the present invention resulted in additional unexpected beneficial results.

Suitable polyalkylene oxides include, inter alia, polyalkylene oxide, such as polyethylene oxide ($(CH_2-CH_2-O)_n$), polypropylene oxide ($(CH(CH_3)CH_2-O)_n$) or a polyethylene/polypropylene oxide copolymer ($(CH_2-CH_2-O)_n-$ $(CH(CH_3)CH_2-O)_m)$. Other straight, branched chain and optionally substituted polyalkylene oxides that would be suitable in the practice of the present invention are well known in the medical field.

Most commonly, the chemical group attached to the hemoglobin is PEG because of its pharmaceutical acceptability and commercial availability. PEGs are polymers of the general chemical formula $HO-(CH_2CH_2O)_n-H$, where n is generally greater than or equal to 4. PEG formulations are usually followed by a number that corresponds to their average molecular weight. For example, PEG-200 has an average molecular weight of 200 and may have a molecular weight range of 190-210. PEGs are commercially available in a number of different forms, and in many instances come pre-activated and ready to conjugate to proteins.

An important aspect of preferred embodiments of the present invention is that PAO attachment takes place when the hemoglobin is in the deoxygenated state. Hemoglobin changes conformation when it is converted from the oxygenated state to the deoxygenated state (i.e., when $O_2$ dissociates from heme.). The $\alpha_1\beta_1$ and $\alpha_2\beta_2$ dimers move as rigid bodies, sliding over one another and rotating the dimer interface by 15 degrees (Dickerson & Geis, *Hemoglobin: Structure, Function, Evolution, and Pathology*, Benjamin/Cummings Publishing Co, Inc., Menlo Park, Calif., (1983)).

It was hypothesized that this change in hemoglobin's quaternary structure, resulting in formation of new hydrogen bonds and/or salt bridges, might expose additional cysteine residues for conjugation with maleimidyl-activated PAO, thus eliminating the necessity for a thiolation step. The maleimide group reacts specifically with sulfhydryl groups when the pH of the reaction mixture is between pH 6.5 and 8.0 and forms a stable thioether linkage that is not reversible (FIG. 1). At neutral pH, maleimides react with sulfhydryls 1,000-fold faster than with amines, but at pH>8.5, the reaction favors primary amines. Maleimides do not normally react with tyrosines, histidines or methionines. Accordingly, by maintaining the pH of the reaction near neutrality (pH 5.5-8.5), or alternatively between 7-7.5, it was believed that maleimide groups would only react with sulfhydryl groups exposed on the surface of the deoxygenated hemoglobin. Quite unexpectedly, as discussed below in the Examples, the maleimide group reacted with lysine and histidine in addition to four reactive cysteines on the tetramer, only two of which were reactive when the hemoglobin tetramer was in the oxygenated state prior to conjugation.

More specifically, the inventors recognized that deoxygenation might expose different reactive residues on the surface. Those possible residues included the thiol reactive groups of β93 Cys, β112 Cys and/or α104 Cys as well the more unlikely possibility that amino or imino groups might become susceptible to maleimidation in the deoxyhemoglobin conformation (e.g. β8 Lys, β17 Lys, β61 Lys, β66 Lys, β2 His, β77 His, β97 His, β146 His, α7 Lys, α11 Lys, α16 Lys, α139 Lys, α20 His, α51 His and α72 His).

The unexpected results achieved with the present invention (i.e. increasing the ability to bind key reactive groups such as β93 Cys thereby increasing the oxygen affinity and lowering the p50 of the HBOC, as well as binding up to 8 PAO on a single hemoglobin molecule in a single reaction) supports the hypothesis that upon deoxygenation of the hemoglobin, certain structural and conformational changes occur exposing reactive sulfhydryl groups, as well as less reactive amino and imino groups that were not previously available in the oxygenated state.

Table 1 lists the amino acids presently identified as having reactive sites for binding N-ethyl maleimide (NEM), a small molecular model for maleimide PEG.

The number of PEGs to be added to the hemoglobin molecule may vary, depending on the size of the PEG. However, the molecular size of the resultant modified hemoglobin should be sufficiently large to avoid being cleared by the kidneys to achieve the desired half-life. Blumenstein, et al., determined that this size is achieved above 84,000 Da molecular weight. (Blumenstein, et al., in *Blood Substitutes and Plasma Expanders*, Alan R. Liss, editors, New York, N.Y., pages 205-212 (1978)). Therein, the authors conjugated hemoglobin to dextran of varying molecular weight. They reported that a conjugate of hemoglobin (with a molecular weight of 64,000 Da) and dextran (having a molecular weight of 20,000 Da) "was cleared slowly from the circulation and negligibly through the kidneys," but increasing the molecular weight above 84,000 did not alter the clearance curves. Accordingly, as determined by Blumenstein, et al., it is preferable that the HBOC have a molecular weight of at least 84,000 Da.

PAO-Hb Conjugate

In one embodiment of the present invention, the HBOC is a "MalPEG-Hb," which stands for hemoglobin to which malemidyl-activated PEG has been conjugated. Such MalPEG-Hb may be further referred to by the following formula:

where Hb refers to hemoglobin, Y' is thiol, amino and/or imino group on the surface of Hb, Y is a succinimide covalent linkage that results from reacting Hb with MalPEG, R is absent or is a linker comprising a alkyl, amide, carbamate or phenyl group (depending on the source of raw material and the method of chemical synthesis) $(-CH_2-CH_2-O)_n$ are the oxyethylene units making up the backbone of the PEG polymer, where n defines the length of the polymer and X is the terminal group, which may include methoxy, protected hydroxyl, acetal, alkenyl, amine, protected amine, methoxy 2-propanol, monoethyl ether, monobenzylether, dibenzylmethylene, and dimethlamine, where m defines number of conjugated PEG molecules/Hb tetramer.

Formulation

The PAO-Hb conjugate of the present invention is formulated by mixing with a suitable diluent and optional excipients. Such PAO-Hb conjugate formulations and their use as HBOCs are known in the literature. Although the concentration of the PAO-Hb conjugates in the diluent may vary according to the application, and in particular based on the expected post-administration dilution, in preferred embodiments, because of the other features of the compositions of the present invention that provide for enhanced oxygen delivery and therapeutic effects, it is usually unnecessary for the concentration to be above 10 g/dl, and is more preferably between 0.1 to 8 g/dl.

Suitable diluents (i.e., one which is pharmaceutically acceptable for intravenous injection) include, for example, proteins, glycoproteins, polysaccharides, and other colloids. It is not intended that these embodiments be limited to any particular diluent. Thus, it is intended that the diluent encompass aqueous cell-free solutions of albumin, other colloids, or other non-oxygen carrying components. In one embodiment, the aqueous solution has a viscosity of at least 2 cP. In other embodiments, the viscosity of the aqueous solution is between 2 and 4 cP. It is contemplated that the present invention also encompasses solutions with a viscosity of 6 cP or greater.

EXPERIMENTS

Experiment 1

Production of Stroma-Free Hemoglobin (SFH)

Outdated packed red blood cells are procured from a commercial source, such as from a local Blood Bank, the New York Blood Center, or the American Red Cross. Preferably, outdated material is received not more than 45 days from the time of collection. All units are screened for viral infection and subjected to nucleic acid testing prior to use. Non-leukodepleted pooled units are leukodepleted by membrane filtration to remove white blood cell. Packed RBCs (pRBCs) are stored at 2-15° C. until further processing. Packed red blood cells are pooled into a sterile vessel in a clean facility. Packed red blood cell volume is noted, and hemoglobin concentration is determined using a commercially available co-oximeter or other art-recognized method.

Red blood cells are washed with six volumes of 0.9% sodium chloride using a 0.45-μm tangential flow filtration, followed by cell lysis by decreasing the concentration of salt and hemoglobin extraction using the same membrane. The cell wash is analyzed to verify removal of plasma components by an ELISA assay for albumin. Lysate is then processed through a 0.16-μm membrane in the cold to purify hemoglobin. Purified hemoglobin is collected in a sterile depyrogenated vessel. The hemoglobin from lysate is exchanged into Ringer's lactate (RL) or phosphate-buffered saline (PBS, pH 7.4) using 6-10 volumes through a 30-kD membrane. The hemoglobin is concentrated to a final concentration of 1.1-1.5 mM (in tetramer). The pH of the solution prepared in RL is adjusted to 7.0-7.6. The purified hemoglobin is then ultrafiltered to remove virus. All steps in this process are carried out at 2-15° C. Additional viral-reduction steps, including solvent/detergent treatment, nanofiltration, and anion Q membrane purification may be performed. The hemoglobin is sterile-filtered through a 0.45 or 0.2-μm disposable filter capsule and stored at 4±2° C. before the chemical modification reaction is performed.

Experiment 2

Production of PEGylated Deoxyhemoglobin (PEG-deoxyHb)

SFH at 0.5 mM (tetramer) in RL or PBS, pH 7.5-9.0, is deoxygenated by gas exchange using a hollow-fiber filter to ≧90% deoxyhemoglobin. The deoxygenated hemoglobin solution is mixed with 5 mM MalPEG dissolved in deoxygenated RL (pH 7.0-7.5) or PBS (pH 7.4) for 3 hours at 30±5° C. with continuous stirring. After 3 hours, an additional 5 mM MalPEG dissolved in deoxygenated RL (pH 7.0-7.5) or PBS (pH 7.4) is added to the reaction mixture with continuous stirring for another 2 hours. After a total of 5 hours of reaction, the mixture is processed by 70-kD tangential flow filtration under deoxygenated conditions, using 10 dia-volumes of RL or PBS to remove excess unreacted reagents and/or hemoglobin. The PEG-deoxyHb is diluted to 4-8 g/dL, and pH is adjusted to 7.4±0.4 using 1N NaOH.

The final PEG-deoxyHb product is collected into a sterile depyrogenated vessel at 4±2° C. The sterilized PEG-deoxyHb is then diluted to 4-6 g/dl in RL, pH adjusted to 7.4±0.2 and aliquoted by weight into sterile glass vials and closed with sterile rubber stoppers with crimped seals in a laminar flow hood under any inert gas like nitrogen or argon and stored at room temperature to −80° C. until use.

Experiment 3

Identification of Sites of Modification and Number of PEGs Conjugated to PEG-deoxyHb The sites of modification were determined using the reaction as described in Experiment 2 using N-ethyl maleimide (NEM) in place of MalPEG because the MalPEG raw material has a wide mass distribution (~5500±750 Daltons) that cannot be resolved by electrospray time-of-flight mass spectrometry (ESI-TOF MS). It should be understood that the reaction of NEM with exposed Hb side groups would result in the same surface modification "pattern" as that achieved with MalPEG. The reaction was followed for up to 44 hours, and the reaction scheme is shown in FIG. 1.

NEM-Hb samples were subjected to SDS-PAGE on Bis-Tris precast gels, with a 4-12% gradient. Gels were stained with Coomassie blue. After staining, NEM-Hb bands were excised and pretreated prior to in-gel trypsin digestion. Reduction of disulfide linkages was performed using 10 mM dithiothreitol, followed by alkylation with 55 mM iodoacetamide (Sigma-Aldrich, St. Louis, Mo.). In-gel digestion with trypsin (Promega, Madison, Wis.) was performed over night at 37° C. at an estimated (1:30) enzyme to substrate ratio in 50 mM ammonium bicarbonate. Tryptic peptides were extracted from the gel using acetonitrile and formic acid and subjected to analysis by LC MS/MS. Separation was performed on a laser pulled 100-μm ID $C_{18}$ column with a tip of <5 μm that was also used as a nanoelectrospray emitter. Gradient elution was used with 0.1% formic acid/acetonitrile as the mobile phases, from 5% to 60% acetonitrile over 90 minutes, and then maintained for an additional 20 minutes with flow rates of ~200 nL/min. MS/MS analysis was performed on a LTQ-DECA (Thermo Electron Corp. Watham, Mass.) and Agilent LC/MSD Trap ion trap mass spectrometer (Agilent, Santa Clara, Calif.). Data-dependent scanning was used to maximize the number of peptides sequenced in the highly complex mixture. This mode of operation uses preset criteria to select unique peptides on-the-fly for undergoing MS/MS. Sequences were searched by MASCOT (Matrix Science, Limited), with Sequest search engine software (University of Washington, WA) using either NCBInr (non-redundant) or SwissProt 55.1 databases. To improve searching efficiency, taxonomic category was limited to mammalian proteins. Only peptides producing good quality fragmentation spectra and scoring higher than the threshold required for 95% confidence level for MASCOT were used for protein identification.

Sites of modification for NEM reactions with deoxyHb for 3, 5, 22, and 44 hours are shown in Table 1. Note that the same experiment performed with oxygenated hemoglobin resulted in NEM modification only to Cys 93.

TABLE 1

Sites of NEM modification with reaction times from 3 to 44 hours given as amino acid residue type, followed in columns by the sequential residue number in human hemoglobin

| | Beta | | | Alpha | | | |
|---|---|---|---|---|---|---|---|
| | Lys | His | Cys | Lys | His | Cys | Val |
| 3 hrs | 8 | 2 | 93 | 7 | 20 | Not Detected | 1 N-term |
| | 17 | 77 | 112 | 11 | | | |
| | 61 | 97 | | 16 | | | |
| | 66 | 146 | | 139 | | | |
| | 144 | | | | | | |

TABLE 1-continued

Sites of NEM modification with reaction times from 3 to 44 hours given as amino acid residue type, followed in columns by the sequential residue number in human hemoglobin

| | Beta | | | Alpha | | | |
|---|---|---|---|---|---|---|---|
| | Lys | His | Cys | Lys | His | Cys | Val |
| 5 hrs | 8 | 2 | 93 | 7 | 20 | Not Detected | 1 N-term |
| | 17 | 77 | 112 | 11 | | | |
| | 61 | 97 | | 16 | | | |
| | | 146 | | 139 | | | |
| 22 hrs | 8 | 2 | 93 | 7 | 20 | Not Detected | 1 N-term |
| | | 77 | 112 | 11 | 51 | | |
| | 61 | 97 | | 16 | 72 | | |
| | 66 | 146 | | 139 | | | |
| | 144 | | | | | | |
| 44 hrs | 8 | 2 | 93 | 7 | 20 | Not Detected | 1 N-term |
| | 17 | 77 | 112 | 11 | 51 | | |
| | 61 | 97 | | 16 | 72 | | |
| | | 146 | | 139 | | | |
| | 144 | | | | | | |

Figure 3:
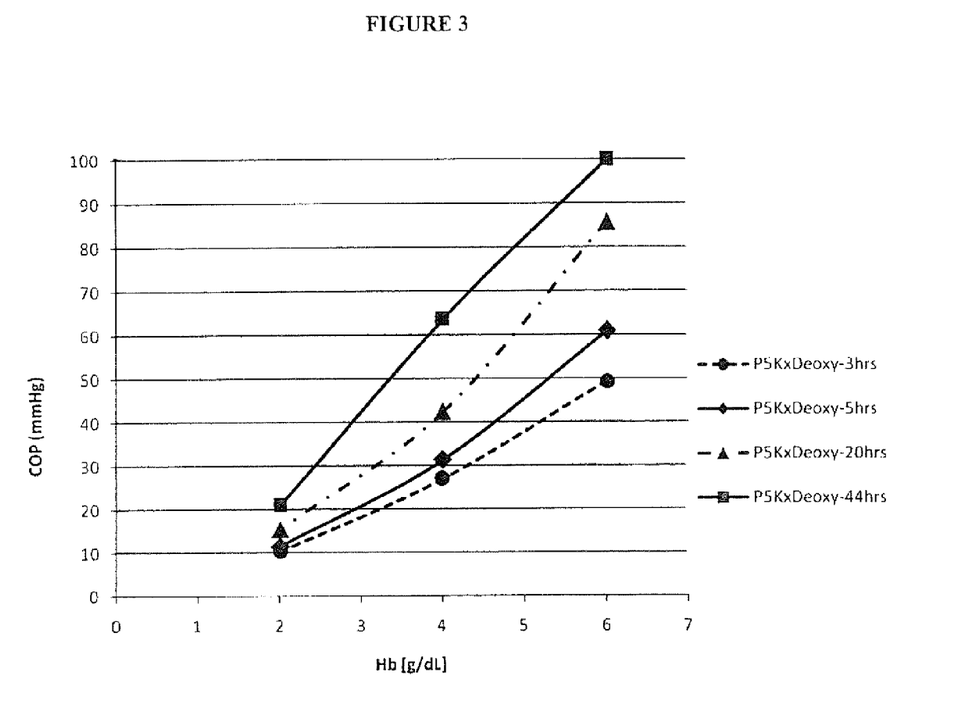
FIG. 3 shows colloidal osmotic pressure (COP) as a function of PEGylation reaction time with deoxyHb, wherein the nomenclature of P5Kx, P5K refers to 5-kD PEG, and x is the number of conjugated PEGs per hemoglobin tetramer (i.e., degree of PEGylation, DOP).

Using these reaction conditions with MalPEG, the degree of PEGylation (DOP) was determined based on the colloidal osmotic pressure (COP) of the PEG-deoxyHb solution (Jan, H., et al., Protein Science Meeting Abstract #430 (2008)) (Table 2). The COPs of these PEG-deoxyHbs at these reaction times are shown in FIG. 3. Thus, PEG-deoxyHb products can be prepared, depending on reaction timing at neutral pH with DOPs ranging from 3 to 5 and with COPs ranging from 27 to 64 mm Hg, respectively.

TABLE 2

DOP and COP as a function of reaction timing.

| Reaction Time (hr) | COP @ 4 g/dL | DOP |
|---|---|---|
| 3 | 27 | 2.9 |
| 5 | 32 | 3.9 |
| 20 | 43 | 4.2 |
| 44 | 64 | 5.4 |

Experiment 4

Physiochemical Analysis of MalPEG-Hb

Methodology for Physiochemical Analysis

Figure 4:
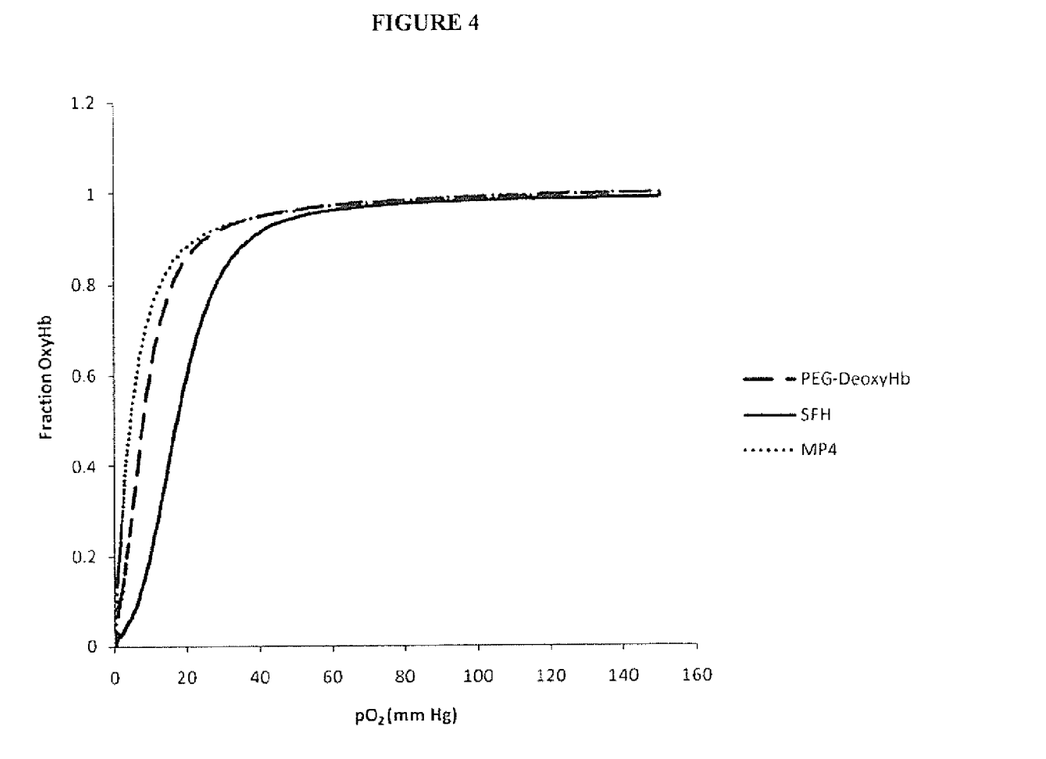
FIG. 4 shows Hb-oxygen equilibrium binding curves (OECs) comparing stroma free hemoglobin (SFH), "MP4" (a PEGylated hemoglobin, Hemospan™, Sangart, Inc. San Diego Calif.), and PEG-deoxyHb. See Table 2 for p50 and Hill number values.

Oxygen equilibrium curves (OECs) were measured using a Hemox-Analyzer TCS (TCS Scientific Corp., New Hope, Pa.). The method is based on dual-wavelength spectrophotometry to calculate hemoglobin saturation as a function of the oxygen partial pressure ($pO_2$), measured using a Clark-type oxygen electrode. Instrument software analysis provides p50 (i.e., the $pO_2$ at which hemoglobin is 50% saturated) and the Hill number, an index of hemoglobin cooperativity. OECs for PEG-deoxyHb compared to MP4 (Hemospan) and SFH are shown in FIG. 4, and p50 and Hill numbers are given in Table 3.

Colloidal osmotic pressure (COP) was determined using a colloid osmometer (Gonotech GmbH, Osmomat 050, Berlin, Germany). The COP of hemoglobin solutions containing unmodified, intra- and intermolecularly cross-linked, or PEG-surface-conjugated hemoglobin have been measured to determine their macromolecular solution properties (Vandegriff, K. D., R. J. Rohlfs, and R. M. Winslow. Colloid osmotic effects of hemoglobin-based oxygen carriers. In Winslow, R. M., K. D. Vandegriff and M. Intaglietta, eds, *Advances in Blood Substitutes Industrial Opportunities and Medical Challenges,* Boston, Birkhäuser, pp. 207-232 (1997)). Tetrameric hemoglobins show nearly ideal solution behavior, whereas hemoglobins conjugated to PEG have significantly higher colloid osmotic activity and exhibit solution non-ideality (Vandegriff, K. D. et al., Biophys. Chem. 69: 23-30 (1997)). The COP of deoxyPEG-Hb solution prepared as described in Experiment 2 is 32 mm Hg (see Table 3).

Human hemoglobin contains 6 thiol groups at cysteine residues. There are also free amino groups available from lysine and imino groups from histidine on the surface of the hemoglobin protein. While maleimide reactivity is many fold greater for sulfhydryl groups, amino and imino groups can also react with maleimides in either one of two ways as shown in FIG. 1. The amine nitrogen can add to the double bond of the maleimide ring via Michael reaction analogous to the addition of —SH or undergo acylation by addition to the carbonyl group followed by ring opening. The methods of the present invention result in 2 to about 8 PEG moieties bound covalently to the deoxygenated hemoglobin. Unexpectedly, even after only three hours, the relatively unreactive lysines efficiently reacted with the NEM.

The number of PEG polymers attached to the surface of hemoglobin in the PEG-deoxyHb process may be determined by correlation with COP at a given hemoglobin concentration as described in Jan, H. Protein Science Meeting Abstract #430 (2008). At a PEG-Hb concentration of 4 g/dL, the fit to a plot of ln COP versus total conjugated PEG mass gives $y=0.0423x+2.5776$, with $R^2=0.9930$. At a COP measured at 4 g/dL, DOP is calculated from the equation where ln COP=y. The number of PEGs attached to PEG-deoxyHb produced under the reaction conditions in Experiment 2 are given in Table 3. Alternatively, for PEG-Hbs using a thiolation reaction followed by PEGylation, such as MP4, DOP can be determined using a dithiopyridine colorimetric assay (Ampulski, R., V. Ayers, and S. Morell, Biocheim. Biophys. Acta 163-169, 1969) to measure the number of available thiol groups on the surface of the Hb tetramer before and after thiolation and then again after Hb PEGylation.

The molecular size and homogeneity of the PEG-deoxyHb and the extent of removal of unreacted MalPEG are determined by analytical liquid size-exclusion chromatography (SEC). Absorbance at 540 nm is used to evaluate hemoglobin and resolves MalPEG-Hb from unreacted hemoglobin by peak position. Absorbance at 280 nm is used to resolve MalPEG-Hb from free MalPEG, which absorbs in the ultraviolet spectrum due to the ring structures in MalPEG.

Free dimer analysis was performed to quantify non-PEGylated residual SFH in the PEG-deoxyHb solution using SEC under forced dissociation conditions using high salt (0.9 M $MgCl_2$). Free dimers were measured by integration of peaks monitored at 540 nm. A comparison of this analysis for SFH, MP4, and PEG-deoxyHb is given in Table 3, where it can be seen that PEG-deoxyHb is more stable against formation of free αβ dimers.

Hydrodynamic size of hemoglobin or PEGylated hemoglobins is measured by dynamic light scattering (Zetasizer Nano-S, Malvern Instruments, Inc., Westborough, Mass.), which measures the diffusion coefficient of particles in solution by their ability to scatter laser light through Brownian motion. Molecular hydrodynamic size is calculated from the Strokes-Einstein equation through the instrument analytical software. Sizes measured for SFH, MP4, and PEG-deoxyHb are given in Table 3.

The physical properties of PEG-deoxyHb compared to SFH and Hemospan (MP4) are shown in Table 3.

TABLE 3

Physical Properties

|  | SFH | PEG-DeoxyHb | Hemospan (MP4) |
|---|---|---|---|
| p50 (mm Hg) | 17 | 8 | 5 |
| Hill number | 2.7 | 1.8 | 1.2 |
| COP (mm Hg) at 4 g/dL | 14 | 32 | 70-80 |
| Number of PEGs/Hb | N/A | 4 | 7-8 |
| MW (kD) | 65 | 87 | 105 |
| Free dimer (%) | 100 | <1 | <2.3 |
| Hydrodynamic size (nm) | 6.2 | 8.3 | 9.0 |

Experiment 5

Stability of PEG-deoxyHb

The experiment to assess the stability of PEG-deoxyHb under deoxygenated conditions was made after conversion of PEG-deoxyHb to the oxygenated form and then re-deoxygenated. Therefore, the starting test solution of PEG-deoxyHb contained ~10% oxyHb. Stability was measured as percent methemoglobin formation over time at room temperature for 96 hours. The percentages of total hemoglobin, percent methemoglobin and oxyhemoglobin were measured using co-oximetry (IL Co-oximetry 682, Global Medical Instrumentation, Inc., Ramsey, Minn.).

The percentage of methemoglobin in the PEG-deoxyHb sample that had 10% starting oxyHb measured over 96 hours increased by a rate of 0.046% $hr^{-1}$ compared to an oxyMP4 sample that increased by a rate of 0.12% $hr^{-1}$.

The examples set forth above are provided to give those of ordinary skill in the art with a complete disclosure and description of how to make and use the preferred embodiments of the compositions, and are not intended to limit the scope of what the inventors regard as their invention. Modifications of the above-described modes for carrying out the invention that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

We claim:

1. A method for preparing a polyalkylene oxide (PAO)-hemoglobin (Hb) conjugate that is useful for delivering oxygen to tissue comprising:
    preparing deoxygenated unthiolated hemoglobin from red blood cells; and
    mixing the deoxygenated hemoglobin with a maleimide-activated PAO to obtain a Hb-PAO conjugate having PAO moieties covalently bound to cysteine, lysine and histidine moieties on the surface of the deoxygenated hemoglobin;
    wherein the PAO-Hb conjugate has a p50 less than native stroma-free hemoglobin from the same animal source when measured under the same conditions.

2. The method according to claim 1 wherein the PAO is polyethylene glycol (PEG) of the formula: HO—$(CH_2CH_2O)_n$—H wherein n is greater than or equal to 4.

3. The method according to claim 2 wherein the PEG molecular weight is 1,000 Daltons to about 20,000 Daltons.

4. The method according to claim 1 wherein the maleimide-activated PAO is maleimide-activated PEG of the formula:

wherein Y is a maleimido moiety, R is absent or is a linker and n is greater than or equal to 4.

5. The method according to claim 4 wherein R if present is an alkyl group having 1 to 6 carbon atoms.

* * * * *